(12) United States Patent
Athalin et al.

(10) Patent No.: US 11,801,208 B2
(45) Date of Patent: Oct. 31, 2023

(54) METHOD FOR TOPICAL PROTECTION AGAINST ATMOSPHERIC POLLUTANT MOLECULES AND/OR FREE RADICALS PRODUCED BY EXPOSURE TO ULTRAVIOLET RADIATION

(71) Applicant: BIONUCLEI, Aix-en-Provence (FR)

(72) Inventors: Han Athalin, Nantes (FR); Jean-Noël Thorel, Larochelle (FR)

(73) Assignee: BIONUCLEI, Aix-en-Provence (FR)

( * ) Notice: Subject to any disclaimer, the term of this patent is extended or adjusted under 35 U.S.C. 154(b) by 514 days.

(21) Appl. No.: 17/251,050

(22) PCT Filed: Jun. 3, 2019

(86) PCT No.: PCT/FR2019/051302
§ 371 (c)(1),
(2) Date: May 4, 2021

(87) PCT Pub. No.: WO2019/229401
PCT Pub. Date: Dec. 5, 2019

(65) Prior Publication Data
US 2021/0251861 A1    Aug. 19, 2021

(51) Int. Cl.
| | |
|---|---|
| *A61K 8/27* | (2006.01) |
| *A61K 8/29* | (2006.01) |
| *A61K 8/34* | (2006.01) |
| *A61K 8/368* | (2006.01) |
| *A61K 8/73* | (2006.01) |
| *A61K 8/81* | (2006.01) |
| *A61Q 17/04* | (2006.01) |

(52) U.S. Cl.
CPC .................. *A61K 8/27* (2013.01); *A61K 8/29* (2013.01); *A61K 8/347* (2013.01); *A61K 8/368* (2013.01); *A61K 8/73* (2013.01); *A61K 8/8176* (2013.01); *A61Q 17/04* (2013.01); *A61K 2800/522* (2013.01)

(58) Field of Classification Search
None
See application file for complete search history.

(56) References Cited

U.S. PATENT DOCUMENTS

2009/0155371 A1    6/2009  Sojka et al.

FOREIGN PATENT DOCUMENTS

WO    2013004777 A1    1/2013

OTHER PUBLICATIONS

International Search Report and Written Opinion of the International Searching Authority for International Application No. PCT/FR2019/051302 dated Nov. 22, 2019.
Halliday, G.M. et al., "Mutation Research/Fundamental and Molecular Mechanisms of Mutagenesis," ScienceDirect, UVA-induced Immunosuppression, vol. 422, Issue 1, Nov. 9, 1998, pp. 139-145.

*Primary Examiner* — Nannette Holloman
(74) *Attorney, Agent, or Firm* — Heslin Rothenberg Farley & Mesiti P.C.

(57) ABSTRACT

A method of providing topical protection against atmospheric pollutant molecules and against ultraviolet (UV) radiation, said method comprising the steps of:
a) forming a polymer matrix that is both repellent and antiadhesive to atmospheric pollutant molecules, by means of a first biocompatible polymer (BP1);
b) under the effect of UV radiation, photocatalytically degrading the pollutant molecules that have penetrated into the polymer matrix by means of first semiconductor colloids (Col-1) grafted covalently with a second biocompatible polymer (BP2), thereby leading to formation of free radicals;
c) neutralizing said free radicals by means of at least 2 antioxidants, namely:
a first antioxidant in the form of second semiconductor colloids (Col-2) grafted covalently with said first antioxidant (AntiOx-1); the second grafted colloids (Col-2) self-regenerating under the action of the UV radiation; and
a second antioxidant (AntiOx-2) that is not in the form of colloids grafted with an antioxidant; and
d) stabilizing the polymer matrix by means of the second antioxidant (AntiOx-2).

20 Claims, 9 Drawing Sheets

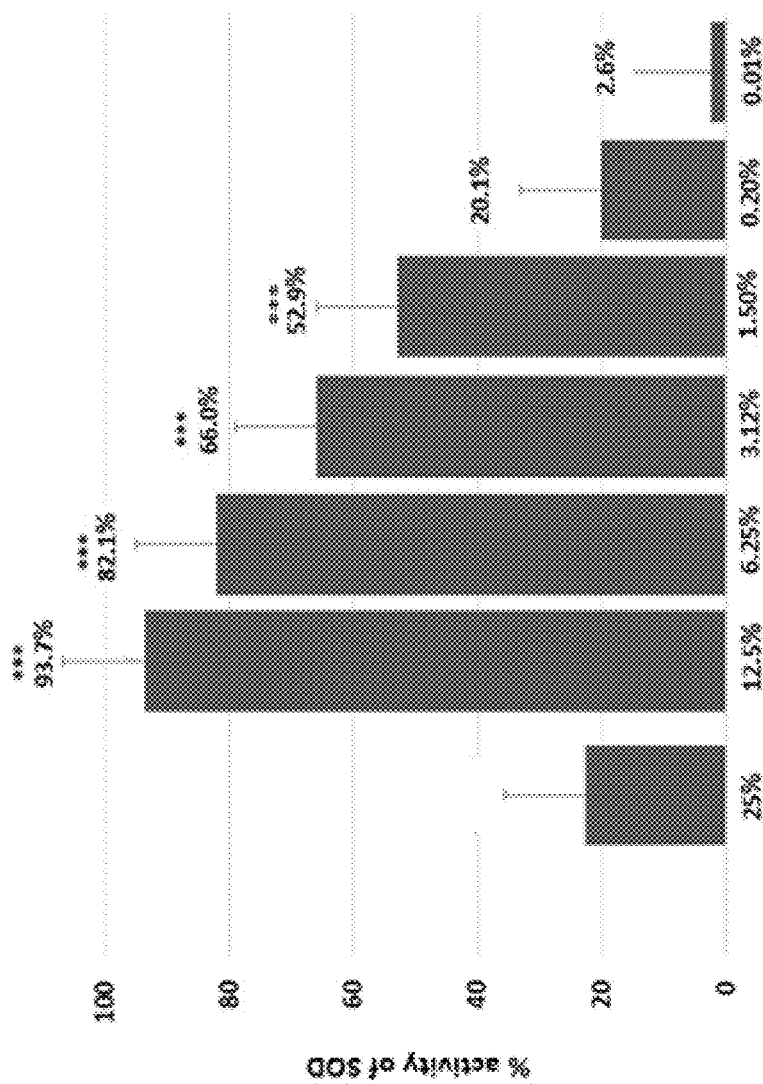

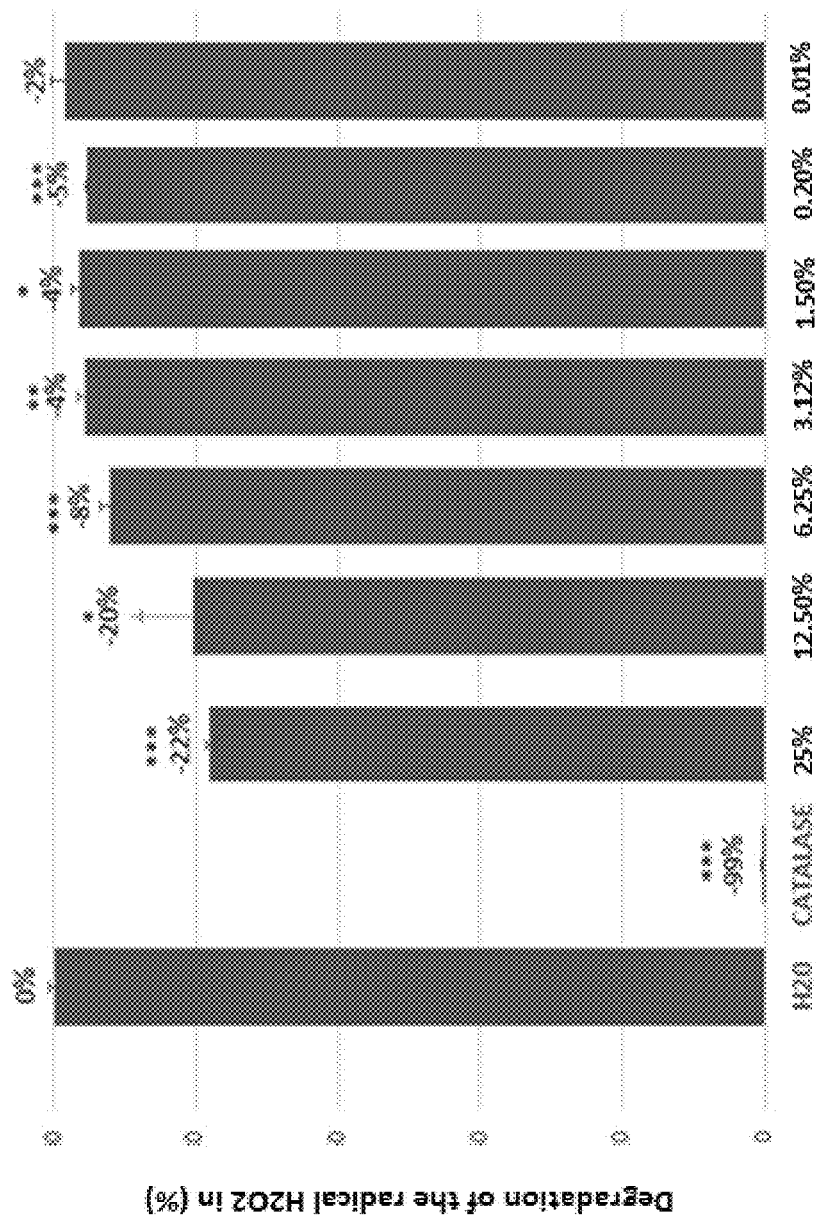

METHOD FOR TOPICAL PROTECTION AGAINST ATMOSPHERIC POLLUTANT MOLECULES AND/OR FREE RADICALS PRODUCED BY EXPOSURE TO ULTRAVIOLET RADIATION

CROSS REFERENCE TO RELATED APPLICATIONS

This application is a national stage filing under section 371 of International Application No. PCT/FR2019/051302 filed on Jun. 3, 2019, and published on Dec. 5, 2019 as WO 2019/229401, which claim priority to French Application No. 1854745, filed on May 31, 2018.

The invention relates to a method of providing topical protection against the harmful effects induced by exposure to pollutant molecules present in the atmosphere and/or by exposure to ultraviolet radiation.

The field of use of the present invention relates, in particular, to cosmetics, and more specifically to the field of anti-pollution protection and sun protection.

The skin is a multifunctional organ, which is also the organ of the human body that extends over the largest area. It performs several fundamental functions, including protection from the outside environment (from impacts, pollution, pathogens, or indeed ultraviolet radiation), thermal regulation, hormone synthesis (vitamin D, and various hormones), or indeed an immune function.

The skin is an organ that is continuously in renewal and that is subjected to the effects of time. As skin ages, the renewal of its cells slows down. The oldest cells accumulate and give the impression of a dull or cloudy complexion and skin that is off-color, and the skin dries out and becomes thinner. In parallel, modifications in the dermis appear, fatty tissue and muscle tissue wastes away and so support is lost. This is the process of skin ageing.

From a molecular viewpoint, skin ageing is related to a degradation in the cell repair mechanisms. It is determined firstly by an individual "biological clock" that is genetically programmed, and secondly by the capacities of the cell to withstand the oxidative damage caused by toxic substances known as "free radicals". This is ageing that is of intrinsic origin.

In parallel, ageing of extrinsic origin is induced by environmental factors and behaviors that are specific to each individual. By way of example, such extrinsic factors include smoking, exposure to natural or artificial atmospheric pollutants, stress, exposure to sun, alcohol consumption, or a sugar-rich diet.

The toxicity of atmospheric pollutants, of natural and artificial origins, is known to be related to their activity as initiators of free radicals.

"Natural atmospheric pollutants" means pollutant particles and molecules that are generated by natural activities (volcanoes, ores, oceans, etc.), such as sulfur dioxide or indeed ozone.

"Artificial atmospheric pollutants" means pollutant particles and molecules that are generated by anthropic activities (factories, motor vehicle engines, etc.), such as polycyclic aromatic hydrocarbons (PAHs), heavy metals, or indeed pesticides.

Some such pollutant molecules can cause inflammation, acceleration of cell ageing, or even certain skin cancers. Among such compounds, persistent organic pollutants (POPs) are some of the atmospheric pollutants that are most dangerous for health. They generally bind to the surface of the skin. After they are absorbed, an oxidative stress phenomenon takes place that causes the acceleration in the skin ageing process.

Similarly, ultraviolet (UV) radiation leads directly or indirectly to appearance of a surplus of pro-oxidants that cause cellular oxidative stress.

A pro-oxidant or a free radical may be defined as a chemical species (molecule or atom) that has an unpaired electron. The most frequent free radicals are hydroxyl radicals (OH·), superoxides ($O_2^{·-}$), nitric oxides (NO·), thiols (RS·), or indeed peroxyls ($RO_2^{·-}$). If the free radical corresponds to an oxygen, the radicals are referred to as "reactive oxygen species" or "ROS", such as singlet oxygen ($^1O_2$) or indeed the superoxide anion ($O_2^{·-}$).

Free radicals are chemical molecules that are unstable due to the unpaired electrons that make them very reactive to the surrounding molecules. A free radical is a pro-oxidant that is neutralized to the detriment of the adjacent molecule, which, in turn becomes a free radical, and so on. The phenomenon is propagated by chain reactions, and this constitutes oxidative stress.

In practice, each pro-oxidant molecule requires at least one electron to be added in order to be stabilized, i.e. in order to be neutralized.

The skin is faced with attack from the surrounding environment on a daily basis. To defend itself against such attack, the human body has developed an effective defense system using antioxidants such as superoxide dismutase (SOD), glutathione peroxidase, or indeed catalase. However, when an excessive quantity of free radicals is generated, an imbalance is established and the antioxidant defense system finds itself overwhelmed, leading to damage being caused to the skin tissue.

The activity of SOD corresponds to a catalytic activity of dismutation of the superoxide anion ($O2^{·-}$), into dioxygen ($O_2$) and hydrogen peroxide ($H_2O_2$). The products of this reaction are considered to be oxygen free radicals even though they do not have unpaired electrons, and they are highly reactive and harmful. By way of example, in the presence of iron, hydrogen peroxide decomposes and produces a hydroxyl radical OH· that is highly toxic for most organic structures. Such products are then considered to be secondary ROS that are produced by the reaction of dismutation of the superoxide anion.

Under physiological conditions, such dismutation is slow and leads to an extended half-life of the superoxide anion, producing harmful oxidation of the biological macromolecules by production of said secondary ROS. Unfortunately, the toxicity of such ROS is considerably greater than that of the superoxide anion.

SOD catalyzes and therefore accelerates the dismutation of the superoxide anion so as to reduce its half-life and thus so as to limit the pro-oxidant effects of the ROS produced secondarily to the reaction of the dismutation of the superoxide anion.

Furthermore, SOD also makes it possible to eliminate other ROS, e.g. $^1O_2$ or ROO.

Indeed, SOD is an enzyme that is capable of reacting with all of the ROS so as to stabilize them and so as to prevent or neutralize their pro-oxidant activity via a multi-electron transfer.

That protein therefore provides a catalytic activity that is essential to the mechanism for eliminating ROS and therefore for eliminating oxidative stress.

In cosmetics, numerous products are designed to produce an antioxidant effect, also known as an "anti-radical" effect, for combating ageing of intrinsic origin and/or of extrinsic origin.

Currently, certain "anti-pollution" compositions have properties of being antiadhesive to pollutant molecules or of storing them, in a film at the surface of the skin, so as to reduce their harmful effects on the skin tissue.

However, the antiadhesive effect has not shown itself to be effective in preventing all of the pollutant molecules from passing through towards the skin. Pollutant particles are thus in contact with the cells of the skin and cause skin ageing.

In particular, and as regards capturing and storing pollutant molecules in a film, it has been shown to be potentially harmful when the film is degraded, under the effect of pH or of heat. Indeed, in such a context, a large concentration of pollutant molecules is in contact with the skin and penetrates it so as to initiate the above-mentioned harmful mechanisms.

In parallel, and for combating the harmful effects associated with exposure to UV radiation, current cosmetic compositions require the use of various organic or inorganic sun filters that are lipophilic or hydrophilic, and/or the use of antioxidants that are not entirely effective.

Protection against oxidative stress, induced, in particular, by pollution and/or UV radiation, is currently based on using the antioxidant virtues of plant extracts, for example. However, such formulations penetrate into the skin, they are complex, and they use a very large number of ingredients, including, among others, solvents and preservatives, the innocuity of which is not always established in the short or long terms.

Therefore, and despite their formulations, it appears that the effectiveness of the vast majority of the solutions proposed is not sufficient.

Currently, no solution that is particularly effective and of simple formulation has been disclosed for protecting against oxidative stress, preferably induced by atmospheric pollution.

The problem that the present invention proposes to solve is that of developing a protection method and a composition for combating the harmful effects of exposure to atmospheric pollutant molecules and/or of exposure to ultraviolet radiation that do not suffer from the above-described drawbacks.

The Applicant has developed a method that, unexpectedly, makes it possible to propose topical protection against the harmful effects of atmospheric pollutant molecules and/or of reactive oxygen species formed by exposure to ultraviolet radiation, and in particular against the phenomenon of oxidative stress.

The advantages of the present invention therefore consist in:
implementing a limited number of compounds;
proposing, for the first time, an antipollution "barrier" effect by antiadhesion and repelling of pollutant molecules;
neutralizing all types of free radicals; and
proposing bioadhesive, antioxidant, and moisturizing properties.

In the description below, the terms "pollutant molecules" and "pollutant particles" are used indiscriminately to describe the same pollutant entities.

The invention firstly provides a method of topically protecting a human being from atmospheric pollutant molecules and from ultraviolet (UV) radiation, the method comprising the steps of:

a) forming, on skin and/or mucous membranes and/or skin appendages, a polymer matrix that is both antiadhesive and repellent to atmospheric pollutant molecules, by means of a first biocompatible polymer (BP1);
b) under the effect of UV radiation, photocatalytically degrading the pollutant molecules that have penetrated into the polymer matrix by means of first semiconductor colloids (Col-1) grafted covalently with a second biocompatible polymer (BP2) that is different from the first biocompatible polymer (BP1), thereby leading to formation of free radicals;
c) neutralizing said free radicals by means of a first antioxidant in the form of second semiconductor colloids (Col-2) grafted covalently with said first antioxidant (AntiOx-1); the second grafted semiconductor colloids (Col-2) self-regenerating under the action of electromagnetic radiation, and preferably UV radiation, by the following mechanism:
regeneration of the first antioxidant (AntiOx-1) by transfer of electrons from the second semiconductor colloids (Col-2) towards said first antioxidant (AntiOx-1); and
regeneration of the second semiconductor colloids (Col-2) by exposure to electromagnetic radiation, and preferably UV radiation; and
d) stabilizing the polymer matrix by means of the second antioxidant (AntiOx-2).

Advantageously, the second antioxidant (AntiOx-2) participates in neutralizing said free radicals, as described by step c).

Preferably, the second antioxidant AntiOx-2 is grafted to the first biocompatible polymer BP1.

By the time they are used, cosmetic products have generally been contaminated either while they are being produced (raw materials, packaging, atmosphere of the premises, UV radiation, handling by staff, etc.), or else by the consumer on being dispensed or taken for use. Unfortunately, such contaminations generate early degradation of the cosmetic product, making it unsuitable for use, or indeed dangerous for the consumer. Such degradations may, in particular, be caused by oxidation of the compounds that is induced by free radicals.

One solution consists in eliminating the free radicals so as to limit the oxidation of the formulation and so as to preserve the product better over time.

In an implementation, the first antioxidant AntiOx-1 and the second antioxidant AntiOx-2 participate in eliminating the ROS produced in the cosmetic formulation, in particular under the effect of exposure to UV radiation.

In detail, the method of the present invention consists in developing a plurality of levels of protection against pollutant particles and against free radicals generated by decomposition of the pollutant particles and/or by UV radiation.

The term "topical protection" is used to mean protecting skin and/or mucous membranes and/or skin appendages.

For more clarity, the term "Col-1/BP2" is used to mean the first semiconductor colloid grafted covalently with a second biocompatible polymer BP2.

For greater clarity, and in the remainder of the description below, the term "Col-2/AntiOx-1" is used to designate the complex formed by the second semiconductor colloid Col-2 of the invention that is grafted covalently with a first antioxidant AntiOx-1.

The antiadhesive and repellent polymer matrix implemented by the method of the invention can be defined as a three-dimensional grid that has a property of being bioadhesive to the skin by means of physical and/or chemical interactions that are non-covalent and reversible. Thus, and after application, the biocompatible polymer BP1 penetrates into the microrelief of the skin and enables chemical bonds to be implemented, e.g. electrostatic forces or hydrogen bonds, by facilitating the bioadhesion phenomenon.

This antiadhesive and repellent polymer matrix is the first element of the protection provided by the invention, and it acts as a "barrier", as a protective film, and as structuring for the matrix medium.

In the sense of the invention, the term "barrier" means an effect that is antiadhesive and repellent to atmospheric pollutant molecules.

In detail, implementing the first biocompatible polymer BP1, which is advantageously a conductive organic polymer, imparts an electronic charge in form of a continuum to the polymer matrix. Conventionally, the electrons at the surface of the polymer matrix tend to be transferred to a lower electron layer in order to recover stability. This transfer is associated with energy being given off, resulting in modifying the surface energy of the polymer matrix. This modification in the surface energy causes the repellent effect of the invention, in particular for repelling pollutant particles. In other words, the reactions generated by the colloids Col-1 and Col-2 and the regeneration of the colloids Col-2 lead to an advantageously continuous modification in the potential energy surface of the first biocompatible polymer.

In the sense of the invention "antiadhesion" is used to mean the action of preventing physical and close attachment between two compounds that generates mechanical resistance to separation of said compounds.

In the sense of the invention, "repellence" means the phenomenon whereby two bodies or two molecules push each other away mutually, and it is an active phenomenon that depends on electronic energy.

The antiadhesive and repellent polymer grid of the invention prevents penetration of the majority of the largest pollutant particles, and preferably those having diameters greater than the diameter of the biocompatible polymer BP1. In parallel, with a proportion of smaller particles having penetrated said matrix, the particles of diameter less than the diameter of the biocompatible polymer BP1 are preferably trapped by the polymer grid.

In the sense of the invention, the term "polymer" means a substance composed of macromolecules, i.e. composed of more than one monomer. Advantageously, the biocompatible polymer BP1 is a polysaccharide. It may, in particular, be chosen from the group comprising pullulan, arabinoxylans, cellulose, chitin, xanthan gum, dextran, welan gum, gellan gum, diutan, and mixtures thereof.

In the sense of the invention, the term "biocompatible" means a compound that is cytocompatible with skin and/or mucous membranes and/or skin appendages, and that has cytotoxicity less than 1% with regard to human cells. In other words, the compound remains almost neutral with respect to cellular viability.

Such cytocompatibility may be assessed by the cell viability test in which the reagent is the tetrazolium salt MTT (3-(4,5-dimethylthiazol-2-yl)-2,5-diphenyl tetrazolium bromide).

The MTT test is a colorimetric method for detecting mitochondrial activity that makes it possible to assess the cytotoxic power of a constituent. It is based on reducing the tetrazolium ring contained in the reagent, by the mitochondrial succinate dehydrogenase of the living and active cells, into formazan This forms a precipitate that is purple in color in the mitochondria. The quantity of precipitate formed is proportional to the quantity of living cells. After incubation of the cells with MTT at 37° C., for about 3 hours, the cells are lysed in 100% DMSO. Assay of the optical density at 550 nm by spectrophotometry makes it possible to know the relative quantity of living cells.

The biocompatible polymer BP1 also makes it possible to improve the dispersion in an aqueous medium of the other compounds implemented in the protection method of the invention. Its use thus makes it possible to obtain a uniform distribution of the complex Col-1/BP2, Col-2/AntiOx-1 and Antiox-2, optionally grafted onto BP1, when the composition is applied to skin and/or mucous membranes and/or skin appendages.

Another element in of the topical protection of the invention consists in implementing photocatalytic action with respect to the pollutant particles that have penetrated the polymer matrix, by means of a complex comprising 2 elements, namely a first semiconductor colloid Col-1 grafted covalently with a second biocompatible polymer BP2.

The colloids Col-1 have particular properties due to them being semiconductor, in particular a photocatalysis property. It is by absorbing photonic energy that the colloid is able to oxidize and to reduce its environment, generally water and oxygen, with the aim of creating reactive species or free radicals. These free radicals degrade the pollutants by breaking the chemical bonds and/or by modifying the degree of oxygenation. This conversion is photocatalyzed, i.e. catalyzed by using the photons available in the UV (200 nm to 400 nm) and visible (400 nm to 800 nm) spectra. This reaction then leads to formation of inert molecules and of free radicals.

It appears from the above that the composition of the invention makes it possible to capture/use the UV radiation for producing a photocatalytic activity, thereby diminishing, limiting, and reducing the quantity of UV radiation that reaches and penetrates the skin.

The grafting of the second biocompatible polymer BP2 onto Col-1 makes it possible to control the photocatalytic activity of the colloids Col-1. It forms a photostabilizer compound that performs the function of deactivator or "quencher" of the activity of the colloids Col-1.

In accordance with a characteristic of the invention, the second biocompatible polymer BP2 is chosen from the group comprising polyvinylpyrrolidone, polyvinyl acetate, polyvinyl alcohol, polyvinyl chloride, styrenics, polyamides, acrylates, and mixtures thereof.

The protection method of the invention also consists in implementing a step of neutralizing the free radicals, in particular those produced by the above-mentioned photocatalysis reaction, so that they do not damage the skin.

This neutralization step requires a complex comprising 2 elements, namely a colloid Col-2 and an antioxidant AntiOx-1 that are grafted together covalently.

In the sense of the invention, "AntiOx-1" means an organic molecule capable of reducing at least one prooxidant by multi-electron transfer, i.e. by transfer of at least 1 electron or H· to a chemical species. In accordance with the invention, this antioxidant carries at least one function capable of reacting with an available function present at the surfaces of the semiconductor colloids to create the complex of the invention.

The antioxidant is grafted by formation of one or more covalent chemical bonds, referred to below as "spacer arm(s)" or "precursor(s)", between the colloids and the antioxidant.

Due to its proximity, the colloid Col-2 is capable of transferring at least one electron to the antioxidant AntiOx- 1, and of doing so as long as the reservoir of Col-2 contains electrons and as long as the antioxidant AntiOx-1 is seeking electrons. The electron transferred in this way makes it possible to regenerate the anti-radical function of the antioxidant. Grafting the antioxidant to the colloid makes it possible to obtain the proximity necessary for transferring at least one electron.

The antioxidant AntiOx-1 may, in particular, be chosen from the group of compounds comprising at least one hydroxyl group (—OH) over at least one aromatic cycle.

Advantageously, the antioxidant AntiOx-1 is a phenol, i.e. a phenyl having at least one hydroxyl group (—OH), or at least one of its derivatives or complexes thereof.

The AntiOx-1 may, in particular be chosen from the group comprising the compounds or their derivatives designated by the following International Nomenclature of Cosmetic Ingredients (INCI) names:

octadecyl di-t-butyl-4-hydroxyhydrocinnamate; pentaerythrityl tetra-di-t-butyl hydroxyhydrocinnamate; 2,6-Bis (1,1-dimethylethyl)-4-methylphenol; bis-ethylhexyl hydroxydimethoxy benzylmalonate; manganese dioxide; colloidal platinum; tert-butylhydroquinone; tetrabutyl ethylidenebisphenol; sodium bisulfite; sodium metabisulfite; thioglycolic acid; thiotaurine; thioctic acid; dilauryl thiodipropionate; aminoethanesulfinic acid; triethyl citrate; sodium erythorbate; sorbityl furfural; erythorbic acid; perillyl alcohol; pyridyloxide t-butylnitrone; ergothioneine; melatonin; acetyl cysteine; cysteine; lysine hydrochloride; carnosic acid; tyrosyl histidine HCl; histidine hydrochloride; pyridoxine serinate; superoxide dismutase; aminopropyl ascorbyl phosphate; ascorbic acid; ascorbic acid polypeptide; ascorbyl dipalmitate; ascorbyl glucoside; ascorbyl linoleate; ascorbyl methylsilanol pectinate; ascorbyl palmitate; ascorbyl tetraisopalmitate; ascorbyl tocopheryl maleate; trisodium ascorbyl palmitate phosphate; disodium ascorbyl sulfate; calcium ascorbate; methylsilanol ascorbate; sodium ascorbate; sodium ascorbyl phosphate; sodium ascorbyl/cholesteryl phosphate; tetrahexyldecyl ascorbate; magnesium ascorbyl phosphate; tocopherol; tocopheryl acetate; tocopheryl linoleate; tocopheryl linoleate/oleate; tocopheryl nicotinate; tocopheryl retinoate; sodium tocopheryl phosphate; dioleyl tocopheryl methylsilanol; potassium ascorbyl tocopheryl phosphate; dodecyl gallate; epigallocatechin gallate EGCG; propyl gallate; ethyl ferulate; ethylhexyl ferulate; chitosan ascorbate; chitosan glycolate; apigenin; tiliroside; alpha-arbutin; arbutin; baicalin; quercetin; quercetin caprylate; isoquercetin=isoquercitrin; isoquercitrin; diethylhexyl syringylidenemalonate; dihydroxy methylchromone; dimethoxy di-p-cresol; dimethylmethoxy chromanol; ethylbisiminomethylguaiacol manganese chloride; hesperidin methyl chalcone; kojic acid; kojic dipalmitate; madecassoside; asiaticoside; magnolol (5,5'-diallyl-2,2'-dihydroxybiphenyl); nordihydroguaiaretic acid; phenylethyl resorcinol; resveratrol; troxerutin (3',4',7-tris(hydroxyethyl) rutin); glucosylrutin; rutin (4H-1-benzopyran-4-one); disodium rutinyl disulfate; tetrahydrobisdemethoxydiferuloylmethane; tetrahydrodemethoxydiferuloylmethane; tetrahydrodiferuloylmethane; tococysteamide; totarol; hydroxydecyl ubiquinone; ubiquinone=coenz Q 10; carotenoids; lycopene; gallic acid; and caffeic acid.

In a particular implementation, the colloid Col-2 is a ZnO or $TiO_2$ colloid, and the AntiOx-1 has an aldehyde group (—CHO) or an acid group capable of reacting with the available functions of the spacer arm providing the covalent bond with the surfaces of said colloids Col-2. In a particular implementation, the antioxidant AntiOx-1 is a phenolic aldehyde or a phenolic acid.

By way of example, the antioxidant AntiOx is, in this situation, 2-hydroxybenzaldehyde, 3-hydroxybenzaldehyde, 4-hydroxybenzaldehyde, 3,4 dihydroxybenzaldehyde, 2,4 dihydroxybenzaldehyde, 4,5 dihydroxybenzaldehyde, and advantageously 3-hydroxybenzaldehyde or 3,4 dihydroxybenzaldehyde (protocatechuic aldehyde).

Advantageously, and also in this implementation, the spacer arm comprises in the range 1 to 8 carbons, and preferably in the range 2 to 4 carbons, and has an alkoxysilane function capable of binding itself covalently to the colloid Col-2 and a function of the hydroxyl type, of the phosphate type, or of the amine type capable of binding itself to the antioxidant AntiOx-1.

Advantageously, the spacer arm is a derivative of silica, advantageously an alkoxysilane, and even more advantageously it is 3-(Aminopropyl)triethoxysilane.

Advantageously, the ratio of the colloid to the silica derivative used for forming the spacer arm lies in the range 1/1 to 10/1, and preferably in the range 2/1 to 3/1.

Advantageously, the antioxidant AntiOx-1 mimics the effect of superoxide dismutase (SOD) that consists in neutralizing all of the ROS, by transfer of at least 1 electron, or indeed by multi-electron transfer.

The second grafted semiconductor colloids Col-2 self-regenerate under the action of electromagnetic radiation, and preferably UV radiation, by the following mechanism:
regeneration of the anti-radical activity of the first antioxidant AntiOx-1 by transfer of electrons from the second colloids Col-2 towards said first antioxidant AntiOx-1; and
regeneration of the second colloids Col-2 by exposure to UV radiation, in particular in the range 280 nm to 400 nm in the UV-A and UV-B range.

This means that the reservoir has the capacity to give electrons to the antioxidant AntiOx-1 indefinitely.

In summary, the colloids Col-2 constitute a reservoir of electrons making it possible to regenerate the anti-radical activity of the antioxidant AntiOx-1 that can then react with as many free radicals as there are electrons available in the colloids and/or oxidize and thus neutralize all of the radical compounds. This effect is related to the proximity between Col-2 and AntiOx-1. Indeed, in the absence of grafting, the antioxidant AntiOx-1 is not regenerated even when colloids Col-2 are present in the reaction medium.

Advantageously, the grafted antioxidant AntiOx-1 is stabler. In other words, the half-life of the antioxidant AntiOx is increased.

The presence of the complexes Col-2/AntiOx-1 makes it possible to avoid formation of radical species secondary to the reaction, in particular singlet oxygen and/or hydrogen peroxide. Conversely, the prior art compositions do not block formation of secondary radical compounds, which is translated by formation of an imbalance between pro-oxidants and antioxidants, producing a "secondary" oxidative stress and cell damage.

In other words, the complex Col-2/AntiOx-1 of the invention neutralizes any primary and/or secondary pro-oxidation activity.

In general, the term "semiconductor colloid" means a compound having an energy difference between the valence band and the conduction band that is small enough for one electron to go from one to the other.

In general, colloids are crystalline particles (non-amorphous form) having semiconductor properties resulting from the ordered stack of molecules constituting them, e.g. ZnO. Such colloids may also be called "quantum dots" or "nanocrystals". They may also be in the form of a dispersion or of a suspension, and advantageously of a suspension, of colloids in an aqueous medium.

The grafting of the biocompatible polymer BP2 and of the antioxidant AntiOx-1 is grafting by forming covalent chemical bonds between the colloids Col-1 and the polymer BP2 and/or between the colloids Col-2 and the antioxidant AntiOx-1.

The concept of grafting, or of functionalization, of colloids is part of the general knowledge of the person skilled in the art. Grafting, or functionalization, corresponds to forming covalent bonds, e.g. between the polymer BP2 and the colloids Col-1 or between the antioxidant AntiOx-1 and the surfaces of the colloids Col-2. The grafting may be performed directly (e.g. functionalization of Col-1 with PVP (BP2), or indirectly via a spacer arm (e.g. functionalization of Col-2 with an alkoxysilane and reaction with a phenolic aldehyde).

The colloids Col-1 and/or Col-2 may be synthesized using conventional techniques, e.g. by a "bottom-up" approach of growing precursors. This type of synthesis, commonly used in the field of nanomaterials, implements a step of nucleation and a step of growth from isolated atoms. It enables the size of the colloids to be controlled.

The semiconductor colloids Col-1 and/or Col-2 are advantageously constituted by at least one element chosen from the group comprising C, Si, Ge, Sn, S, Se, Te, B, N, P, As, Al, Sb, Ga, In, Cd, Zn, O, Cu, Cl, Pb, Tl, Bi, Ti, U, Ba, Sr, Li, Nb, La, I, Mo, Mn, Ca, Fe, Ni, Eu, Cr, Br, Ag, Pt, Hg, and combinations thereof.

In advantageous manner, the semiconductor colloids Col-1 and/or Col-2 of the invention comprise two or three of these elements.

In a particular implementation, the semiconductor colloids Col-1 and/or Col-2 are colloids of zinc oxide, ZnO.

In another particular implementation, the semiconductor colloids Col-1 and/or Col-2 are colloids of titanium oxide, $TiO_2$.

In another particular implementation, the semiconductor colloids Col-1 and/or Col-2 are colloids of bismuth oxide, $Bi_2O_3$.

In general, the colloids Col-1/BP2 and/or Col-2/AntiOx-1 have a mean size in the range a few nanometers to a few tens of nanometers.

Thus, the colloids Col-1/BP2 and/or Col-2/AntiOx-1 have a size lying advantageously in the range 0.5 nm to 1000 nm, more advantageously in the range 10 nm to 100 nm, and even more advantageously about 30 nm, the size being measured by XRD.

The XRD (X-ray diffraction) technique is a technique conventionally used for measuring the size of crystals in the solid state.

The term "size" means the largest dimension of the colloids, e.g. the diameter when the colloids are of spherical shape. It is the mean size of grafted colloids. However, the size of the non-grafted colloids Col-1 and Col-2 generally also lies in the above-indicated ranges of values. Where necessary, the person skilled in the art is capable of adapting the size of the non-grafted colloids Col-1 and Col-2.

The colloids Col-1 and/or Col-2 and/or Col-1/BP2 and/or Col-2/AntiOx-1 are advantageously of spherical shape.

Naturally, the grafting is not limited to grafting a single polymer chain or to grafting a single antioxidant molecule. It is grafting of a multitude of molecules of at least one type of polymer or of at least one type of antioxidant to each nanocrystal.

The colloids are not doped. Optionally, they may include a transition metal that is introduced during synthesis of the colloids.

The term "doping" means incorporation of an element into a material that is already formed. Incorporating an element while a material is being synthesized, i.e. upstream from the formation of the material, is not considered as being doping.

In the method of the present invention, a second antioxidant AntiOx-2 is implemented and can participate in neutralizing the reactive species brought by the pollutants or by decomposition products thereof, and is not in the form of colloids grafted with an antioxidant.

Advantageously, the second antioxidant AntiOx-2 is a phenol, i.e. a phenyl having at least one hydroxyl group (—OH), or at least one of its derivatives, or complexes thereof.

The AntiOx-2 may, in particular be chosen from the group comprising the compounds or their derivatives designated by the above-listed INCI names.

The grafting may be performed by esterification between a hydroxyl group (—OH) of the first biocompatible polymer BP1 and an acid function (R—CO—OH) of said second antioxidant AntiOx-2. By way of example, the antioxidant AntiOx-2 may be gallic acid.

In another implementation, the antioxidant AntiOx-2 may be caffeic acid, 3-hydroxybenzaldehyde or 2-hydroxybenzaldehyde, or 4-hydroxybenzaldehyde or 3,4 dihydroxybenzaldehyde, or 2,3 dihydroxybenzaldehyde, or 4,5 dihydroxybenzaldehyde.

Advantageously, the antioxidants AntiOx-1 and AntiOx-2 are identical.

Said first antioxidant AntiOx-1, and optionally said second antioxidant AntiOx-2, react directly with the free radicals coming from the degradation of the pollutants or from exposure to UV radiation, by trapping or "scavenging" the electrons. These free radicals are neutralized and do not produce any oxidative stress.

The antioxidant AntiOx-2 also makes it possible to protect the biocompatible polymer BP1 from any degradation that might result from the freeing of radicals that is generated by the photocatalytic activity of Col-1/BP2.

In a preferred implementation, the second antioxidant AntiOx-2 is grafted to the first biocompatible polymer BP1.

This grafting makes it possible to protect the formulation in addition to the protection brought to the skin by the antioxidant action. Thus, the formulation, and more precisely the first biocompatible polymer BP1, is protected from the potential degradation due to the photocatalytic effect produced by the first colloids grafted with a second biocompatible polymer BP2, i.e. Col-1/BP2, as described above.

The invention also provides a topical cosmetic composition suitable for implementing the method as defined above, and comprising:
  a first biocompatible polymer BP1;
  first semiconductor colloids Col-1 grafted covalently with a second biocompatible polymer BP2;
  a first antioxidant AntiOx-1 in the form of second semiconductor colloids Col-2 grafted covalently with said first antioxidant AntiOx-1; and
  a second antioxidant (AntiOx-2) that is not in the form of colloids grafted with an antioxidant.

Thus, the second antioxidant AntiOx-2 is not in the form of an antioxidant grafted to colloids.

Advantageously, the second antioxidant AntiOx-2 is grafted to the first biocompatible polymer BP1 (BP1/AntiOx-2).

In an implementation, the semiconductor colloids Col-1 and/or Col-2 are advantageously constituted by at least one element chosen from the group comprising C, Si, Ge, Sn, Se, Te, B, N, P, As, Al, Sb, Ga, In, Cd, Zn, O, Cu, Cl, Pb, Tl, Bi, Ti, U, Ba, Sr, Li, Nb, La, I, Mo, Mn, Ca, Fe, Ni, Eu, Cr, Br, Ag, Pt, Hg, and combinations thereof.

Advantageously, the semiconductor colloids Col-1 and/or Col-2 of the topical composition are colloids of zinc oxide, ZnO.

Advantageously, the semiconductor colloids Col-1 and/or Col-2 of the topical composition are colloids of titanium oxide, $TiO_2$.

Advantageously, the semiconductor colloids Col-1 and/or Col-2 of the topical composition are colloids of bismuth oxide, $Bi_2O_3$.

In a preferred implementation, the composition comprises:
the first biocompatible polymer BP1 that is a polysaccharide;
the first and second colloids that are colloids of zinc oxide, ZnO, or of titanium dioxide, $TiO_2$, or of bismuth oxide $Bi_2O_3$;
the second biocompatible polymer BP2 that is chosen from the group comprising polyvinylpyrrolidone, polyvinyl acetate, polyvinyl alcohol, polyvinyl chloride, styrenics, polyamides, acrylates, and mixtures thereof; and
the first and second antioxidants, AntiOx-1 and AntiOx-2, that correspond to a phenol or to a derivative thereof, advantageously a phenolic aldehyde or a phenolic acid or complexes thereof, the first antioxidant advantageously being different from the second antioxidant.

Advantageously, the polysaccharide is pullulan.

Preferably, the second biocompatible polymer BP2 is polyvinylpyrrolidone and the first antioxidant AntiOx-1 is 3-hydroxybenzaldehyde or 3,4 dihydroxybenzaldehyde.

In a particular implementation, the second semiconductor colloids Col-2 grafted covalently with a first antioxidant AntiOx-1 are formed of:
second colloids Col-2 that are colloids of zinc oxide, ZnO, or of titanium oxide, $TiO_2$;
a first antioxidant AntiOx-1 that is a phenolic aldehyde or a phenolic acid; and
a covalent grafting in the form of a spacer arm positioned between Col-2 and AntiOx-1, the spacer arm comprising in the range 1 to 8 carbons, and preferably in the range 2 to 4 carbons, and having an alkoxysilane function capable of binding itself covalently to the colloid Col-2 and a function of the hydroxyl type, of the phosphate type, or of the amine type capable of binding itself to the antioxidant AntiOx-1.

Advantageously:
the first antioxidant AntiOx-1 is chosen from the group comprising 2-hydroxybenzaldehyde, 3-hydroxybenzaldehyde, or 4-hydroxybenzaldehyde, 3,4 dihydroxybenzaldehyde, 2,4 dihydroxybenzaldehyde, 4,5 dihydroxybenzaldehyde; and
the spacer arm is advantageously 3-(aminopropyl)triethoxysilane.

In another implementation, the second biocompatible polymer is polyvinylpyrrolidone and/or the first antioxidant is phenol or a derivative of phenol, or complexes thereof, preferably 2-hydroxybenzaldehyde, 3-hydroxybenzaldehyde or 4-hydroxybenzaldehyde or 3,4 dihydroxybenzaldehyde, or 2,3 dihydroxybenzaldehyde, or 4,5 dihydroxybenzaldehyde.

Advantageously, AntiOx-2 is gallic acid.

In a preferred implementation, the composition comprises:
the first biocompatible polymer BP1 that is pullulan, advantageously grafted with gallic acid, and that represents in the range 0.1% by mass to 20% by mass, relative to the mass of the composition, advantageously in the range 0.5% by mass to 10% by mass, and preferably in the range 0.8% by mass to 5% by mass;
the first semiconductor colloids that are zinc oxide colloids, grafted with PVP (ZnO/BP2) and that represent in the range 0.1% by mass to 30% by mass, relative to the mass of the composition, advantageously in the range 1% by mass to 20%, and preferably in the range 5% by mass to 9% by mass; and
the second semiconductor colloids are colloids of zinc oxide grafted with a phenolic aldehyde or a phenolic acid or complexes thereof, and represent in the range 0.1% by mass to 10% by mass, relative to the mass of the composition, advantageously in the range 0.5% by mass to 5% by mass, and preferably in the range 0.6% by mass to 2% by mass.

Furthermore, the composition may further comprise at least one additive chosen from the group comprising humectant agents, viscosity control agents, and water.

Advantageously, the humectant agent is chosen from the group comprising glycerol, urea, lactic acid and mixtures thereof.

The composition advantageously includes in the range 0.1% to 20% of humectant agent, preferably glycerol, by mass, relative to the mass of the composition, advantageously in the range 1% to 10%, and preferably in the range 2% to 6%.

The humectant agent makes it possible to prevent the composition from drying out too rapidly once it has been applied to the skin. It also contributes to moisturizing the skin. It may also contribute to controlling the viscosity of the composition, and, to this end, to optimizing spreading of the composition on the skin.

Advantageously, the stabilizer may be chosen from the group comprising guar gum, xanthan gum, or mixtures thereof.

The composition advantageously includes in the range 0.1% by mass to 20% by mass of stabilizer, preferably guar gum, relative to the mass of the composition, advantageously in the range 0.2% by mass to 10% by mass, and preferably in the range 0.5% by mass to 5% by mass.

The stabilizer makes it possible to control the viscosity of the composition.

Advantageously, the composition further comprises water. The composition advantageously includes in the range 30% by mass to 99% by mass of water relative to the mass of the composition, advantageously in the range 50% by mass to 90% by mass, and preferably in the range 70% by mass to 85% by mass.

In a preferred implementation, the composition of the invention consists of:
pullulan as the first biocompatible polymer BP1, advantageously grafted with gallic acid, and preferably in the range 0.8% by mass to 5% by mass, relative to the mass of the composition;

zinc oxide colloids grafted with PVP as first colloids (ZnO/BP2 or TiO$_2$/BP2 or Bi$_2$O$_3$/BP2), preferably in the range 5% by mass to 9% by mass, relative to the mass of the composition;

zinc oxide or titanium oxide or Bi$_2$O$_3$ colloids grafted with a phenolic aldehyde or with a phenolic acid as second colloids (ZnO/AntiOx-1 or TiO$_2$/AntiOx-1), and preferably in the range 0.6% by mass to 2% by mass, relative to the mass of the composition;

glycerol as humectant agent, preferably in the range 2% by mass to 6% by mass, relative to the mass of the composition;

guar gum as stabilizer, preferably in the range 0.5% by mass to 5% by mass, relative to the mass of the composition; and water, preferably in the range 70% by mass to 85% by mass, relative to the mass of the composition.

Advantageously, the composition of the invention is an aqueous formulation that has shear-thinning, quick-drying, and stability properties, and is advantageously free of parabens and/or of organic solvents.

In an implementation, the composition of the invention is for topical use, e.g. a cosmetic composition for non-therapeutic use. This composition is advantageously hydrophilic, micellar or a Pickering emulsion (i.e. a reverse form of a micellar composition).

The composition of the invention may also be implemented as a makeup base.

The manner in which the invention may be implemented and the resulting advantages appear more clearly from the following examples of implementations, which are given by way of non-limited indication and with the support of the accompanying figures.

DESCRIPTION OF THE FIGURES

FIGS. 8A and 8B show the activity mimicking the SOD effect of the antioxidant AntiOX-1 compared with the superoxide anion and with hydrogen peroxide;

EXAMPLES OF IMPLEMENTATIONS OF THE INVENTION

Figure 1:
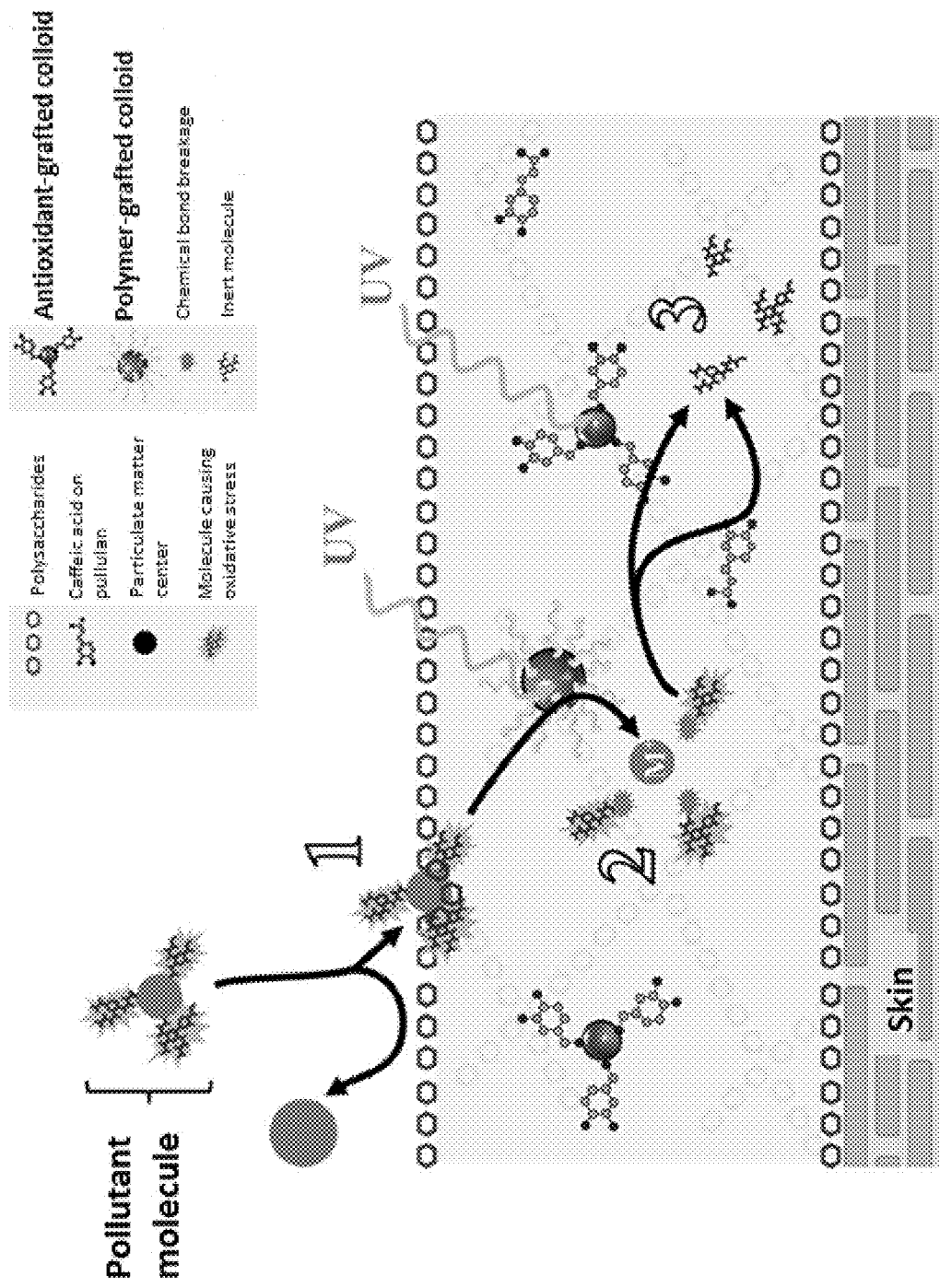
FIG. 1 shows the mechanisms of action of the composition of the invention.

FIG. 1 shows the mechanisms of action of the composition of the invention.

1/ Synthesis of the colloids Col-1 and Col-2
The Percentages are Given by Weight of the Composition
1.1/ With Col-1 and Col-2=ZnO A zinc oxide precursor, such as anhydrous zinc acetate (2%) and sodium hydroxide (1.5%), was mixed with a solvent or with a mixture of solvents comprising ethanol (85%) and diethylene glycol (8%) and sealed in an autoclave. The solvent may also be benzyl alcohol, phenol, oleyl alcohol, butanol, propanol, isopropanol, water, tetrahydrofuran, ethanol, methanol, acetonitrile, toluene, PGMEA, PGPE, PGME, 2-methyl-1-propanol, or triethylene glycol monomethyl ether.

The reaction medium was placed under mechanical agitation at 60° C. for about 30 minutes, until the salts had dissolved. Water (2%) was then added. Cloudiness was observed that marked the start of formation of the particles. The reaction was kept at 65° C. for one and a half hours.

Zinc oxide nanocrystals that were spherical and 7 nm in diameter were collected.

1.2/ With Col-1 and Col-2=TiO$_2$

Under the same conditions as in the preceding example, the same antioxidant was grafted onto rutile titanium dioxide. 5 g of rutile titanium dioxide was dispersed in a mixture of 950 mL ethanol and 50 mL diethylene glycol and was then sealed in an autoclave.

The reaction medium was placed under mechanical agitation at 60° C. for about 30 minutes, until the salts had dissolved. Water (2%) was then added. Cloudiness was observed that marked the start of formation of the particles. The reaction was kept at 65° C. for one and a half hours.

Titanium dioxide nanocrystals that were spherical and 7 nm in diameter were collected.

2/ Preparation of the colloids Col-2/AntiOx-1
2.1/ ZnO/3-hydroxybenzaldehyde

Colloids of the invention were prepared using the zinc oxide (ZnO) colloids obtained above and a precursor or spacer arm of the antioxidant 3-hydroxybenzaldehyde. Particles of ZnO/3-hydroxybenzaldehyde were thus obtained. In practice, the nanocrystals formed above were functionalized in situ with (3-Aminopropyl)triethoxysilane (0.5%). On addition, the solution cleared slightly. This functionalization was performed for an additional 3 hours. Finally the antioxidant 3-Hydroxybenzaldehyde (1.5%) was added. The reaction was maintained for 9 hours.

The reactor was then cooled to ambient temperature. The particles were collected and centrifuged at 3000 revolutions per minute (rpm) for 15 minutes. They were then washed in ethanol, and then centrifuged again. Finally, the particles were dispersed to the desired concentration in water (mass concentration in the range 10% to 15%). The small size of the ZnO particles made it possible to have a larger area to cover and thus to graft a larger number of antioxidant molecules to the surface of each of the particles.

The diameter of the ZnO colloids was measured by means of an X-ray diffractometer (XRD). The wavelength produced by the diffractometer corresponded to the Cu-Kα line equal to 1.54 Å. The other parameters used corresponded to an acceleration voltage of 40 kV, to an electric current of 40 mA, and to a Bragg-Brentano geometry.

Figure 2:
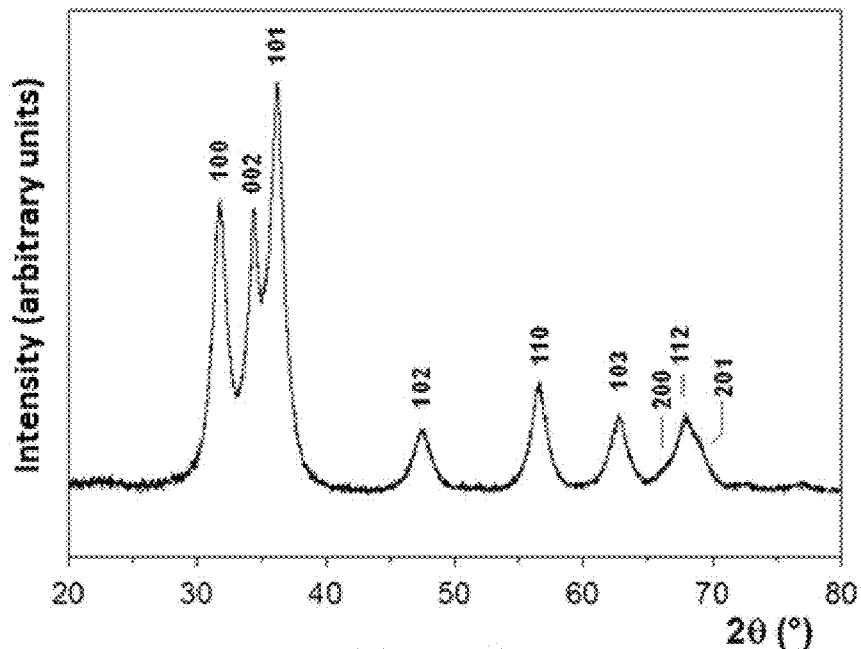
FIG. 2 shows the X-ray diffraction pattern of the ZnO colloid after functionalization with the antioxidant. The spectrum lines are indexed with the planes corresponding to the hexagonal ZnO structure.

The X-ray diffraction patterns were measured on powder with an XRD of Cu-Kα source in transmission. The X-ray diffraction pattern of colloids before functionalization (grafting) with the antioxidant is shown in FIG. 2.

2.2/ TiO$_2$/3 hydroxybenzaldehyde

In practice, the nanocrystals formed above were functionalized in situ with (3-Aminopropyl)triethoxysilane. In practice, 5 mL of water was added, and then 8 mL of (3-Aminopropyl)triethoxysilane. The mixture was left to be agitated for two hours, and then 5 g of 3-hydroxybenzaldehyde was added, and the mixture was left to be agitated and heated at 65° C. for 9 hours. The mixture was then cooled to ambient temperature. The particles were collected and centrifuged at 3000 rpm for 15 minutes. They were then washed in ethanol, and then centrifuged again. Finally, the particles were dispersed to the desired concentration in water.

2.2/ TiO$_2$/3,4 dihydroxybenzaldehyde

In practice, the nanocrystals formed above were functionalized in situ with (3-Aminopropyl)triethoxysilane. In practice, 5 mL of water is added, and then 8 mL of (3-Aminopropyl)triethoxysilane. The mixture was left to be agitated for two hours, and then 5 g of 3,4 dihydroxybenzaldehyde was added, and the mixture was left to be agitated and heated at 65° C. for 9 hours. The mixture was then cooled to ambient temperature. The particles were collected and centrifuged at 3000 rpm for 15 minutes. They were then washed in ethanol, and then centrifuged again. Finally, the particles were dispersed to the desired concentration in water.

3/ Preparation of the Colloids Col-1/BP2 (PVP)

3.1/ Method of Preparing the Colloids ZnO/BP2

The colloids were grafted conventionally, e.g. in a solution of water and of ethanol containing the colloids to be functionalized and the functionalizing polymer (BP2).

In practice, the nanocrystals formed above were functionalized in situ by PVP (2% by weight) dissolved in ethanol (solution at 20% by mass). The reaction was maintained for 12 hours. The reactor was then cooled to ambient temperature. The particles were collected and centrifuged at 3000 rpm for 15 minutes. They were then washed in ethanol, and then centrifuged again. Finally, the particles were dispersed in water and heated under reflux for 2 hours.

The small size of the ZnO particles made it possible to have a larger area to cover and thus to graft a larger number of antioxidant molecules to the surface of each of the particles.

The X-ray diffraction patterns were measured on powder with an XRD of Cu-Kα source in transmission.

3.2/ Method of Preparing the Colloids TiO$_2$/BP2

The same method as in 3.1 was repeated.

3/ Preparing the Complex AntiOx-2/BP1 (Gallic acid/pullulan)

0.001-0.01 mmol of pullulan was dissolved in 50-100 mL of N,N-Dimethylformamide. The mixture was heated at 40-80° C. for 5-30 minutes under a flow of inert gas.

500-5000 equivalents of gallic acid and 500-5000 equivalents of Dicyclohexylcarbodiimide previously dissolved in 5-20 mL of N,N-Dimethylformamide was added to the solution. The reaction was kept at 70° C. under a flow of inert gas for 24-72 hours.

The product was precipitated by adding 2-20 times the reaction volume in ethanol and then collected by filtration.

4/ Determining the Antioxidant Activity of the Colloids ZnO/AntiOx-1

4.1. Kinetic Time

The rate of action of the colloids Col/AntiOx was estimated by measuring the decomposition kinetics of 2,2-diphenyl-1-picrylhydrazyl (DPPH).

DPPH is a molecule that keeps its free radical capacity stably. This radical species absorbs light at 520 nm (purple color of the solution) and becomes colorless or pale yellow after neutralization by an antioxidant. It is thus possible to monitor the neutralization reaction by measuring the intensity of the measurement of absorption of the radical DPPH as a function of time.

For that purpose, two solutions in ethanol were prepared as follows:
- a control solution containing DPPH at a $[DPPH]_0$ concentration of 0.1 mol/L; and
- a test solution containing DPPH at a $[DPPH]_0$ concentration of 0.1 mol/L and an antioxidant at a concentration such that 90% of the DPPH was consumed after 2 hours (as determined based on the $CI_{50}$ measurements).

Absorbance was measured by means of a UV/vis/NIR spectrometer. 2.5 mL of solution was poured into a polystyrene vessel (optical path=1 cm). The UV/visible absorption spectrum from 310 nm to 700 mm was measured for 300 seconds. The value of the absorbance at 520 nm made it possible to determine the concentration of radical DPPH at a given time using the Beer-Lambert equation:

$$A_{520\,nm}(\tau) = \varepsilon_{DPPH} \cdot 1 \cdot [DPPH]_\tau$$

In accordance with that equation, A corresponds to the measured absorbance, $\varepsilon_{DPPH}$ corresponds to the mass coefficient of DPPH, 1 (cm) corresponds to the optical path through the sample, and $[DPPH]_\tau$ (g/L) corresponds to the mass concentration of the sample.

The curves obtained were honed using a kinetic model that made it possible to go back to the reaction rate or "kinetic" constant κ and the half-life constant $\tau_{1/2}$ of the rection.

Figure 3:
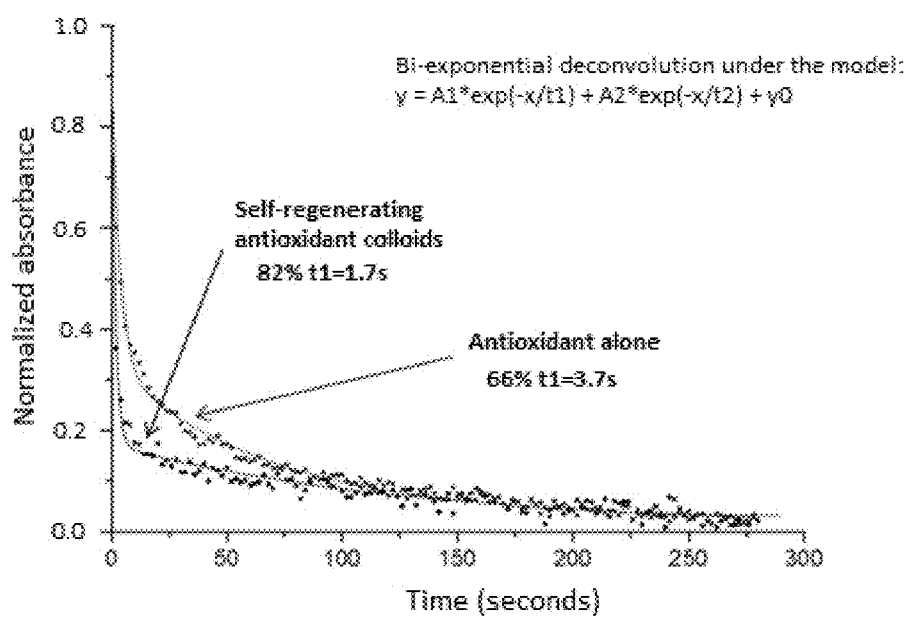
FIG. 3 shows the DPPH kinetics for colloids functionalized with the antioxidant (Col-2/AntiOx-1) and for the antioxidant alone.

The graph showing the rate of action of the colloids functionalized with an antioxidant (ZnO/3-hydroxy benzaldehyde) and the rate of action of the free, i.e. not grafted, antioxidant (3-hydroxy benzaldehyde) is shown in FIG. 3.

The results show that the complex ZnO/3-hydroxy benzaldehyde reacted faster with the DPPH than the free 3-hydroxy benzaldehyde.

5/ Assessing the Regeneration of the Antioxidant Activity of the Colloids ZnO/AntiOx-1

5.1/ Assessment Over Time

A stock solution of ABTS (2,2'-azino-bis(3-ethylbenzothiazoline-6-sulfonic) acid) at 8 mM was incubated, at equal volume, with a solution at 3 mM comprising metmyoglobin and hydrogen peroxide so as to produce an ABTS radical cation. The solution obtained was diluted with phosphate buffer (0.2 M, and pH 7.4) containing 150 mM of NaCl so as to obtain an absorbance of 1.5 at 734 nm.

Samples of 30 μL of ZnO/3-hydroxy benzaldehyde (example 2/) dispersed at 240 g/L in water were added to 2970 μL of the 0.07 mM ABTS cation solution in water, and then placed under agitation in the dark.

After 30 minutes of incubation, the ABTS was totally degraded.

The solution obtained after this step of degradation of the entire ABTS substrate was separated, a fraction of the solution being placed in the dark, and the remaining fraction being placed under UV irradiation. After 30 minutes of exposure (in the dark or under UV), 30 μL of a concentrated solution of ABTS (7 mM) was added, and then the solutions were, once again, placed in the dark under agitation for 5 hours. The absorption was then measured every 30 minutes.

Figure 4:
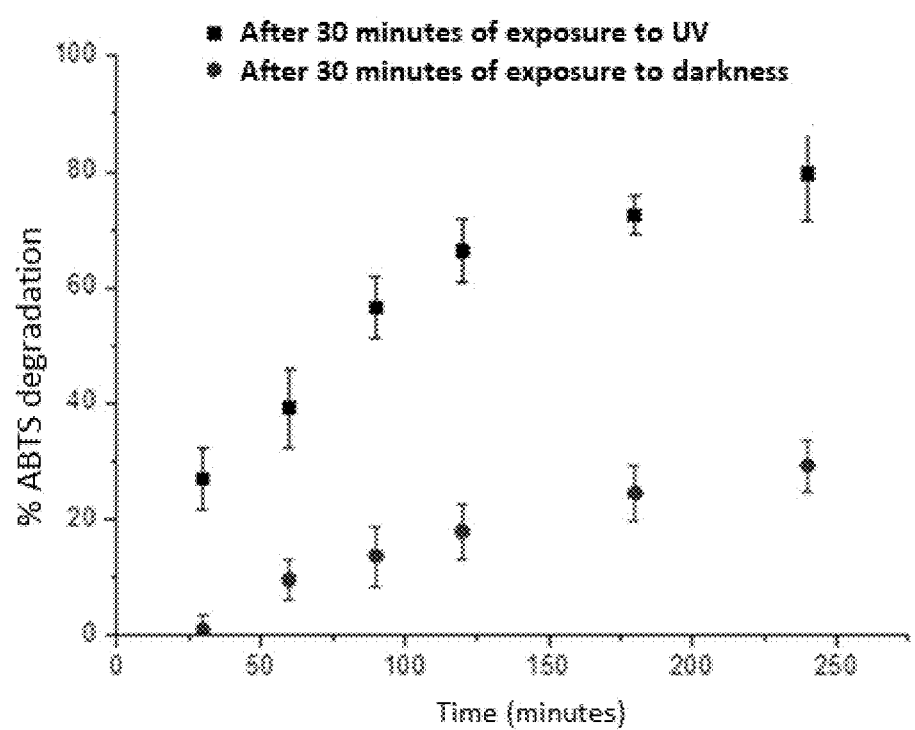
FIG. 4 shows the percentage of ABTS substrate degraded by the colloids of the invention as exposed to UV rays or as kept in the dark.

The data is shown in FIG. 4.

The results show that the solution containing ZnO/3-hydroxy benzaldehyde colloids and exposed to UV radiation has an ABTS degradation capacity that is considerably greater than the solution containing ZnO/3-hydroxy benzaldehyde colloids that remained in the dark. The activity of the ZnO/3-hydroxy benzaldehyde colloids that remained in the dark corresponds to the residual anti-radical activity inherent in the ZnO/3-hydroxy benzaldehyde complex. Thus, after 120 minutes, 65% of the ABTS was degraded by the solution that had been exposed to UV radiation, as compared with 18% for the solution that remained in the dark.

In conclusion, the ZnO/3-hydroxy benzaldehyde colloids of the invention have the capacity to regenerate their antioxidant activity when they are exposed to UV radiation.

6/ Assessment of the Protective Power of the Composition of the Invention Against the Effects of UV Radiation Five main harmful effects are conventionally recognized as being related to harm caused by exposure to UV radiation:
generation of free radicals;
inflammatory reaction;
oxidation of the melanins;
mutation of the DNA; and
immunosuppression.

Using an approach similar to that in the work by Halliday et al. (Halliday, G. M., Bestak, R., Yuen, K. S., Cavanagh, L. L., & Barneston, R. S. C. (1998). UVA-induced immunosuppression. *Mutation Research*, 422, 139-145), Gaussian or bi-Gaussian models (depending on the parameter studied) were established for describing the phenomena caused by the harmful effects induced by UV radiation.

The data was obtained in compliance with the conventional experiment protocols, known to the person skilled in the art and complying with the ISO standards for assessing sun protection. The data was normalized by the Normalized Solar Irradiance.

Figure 5:
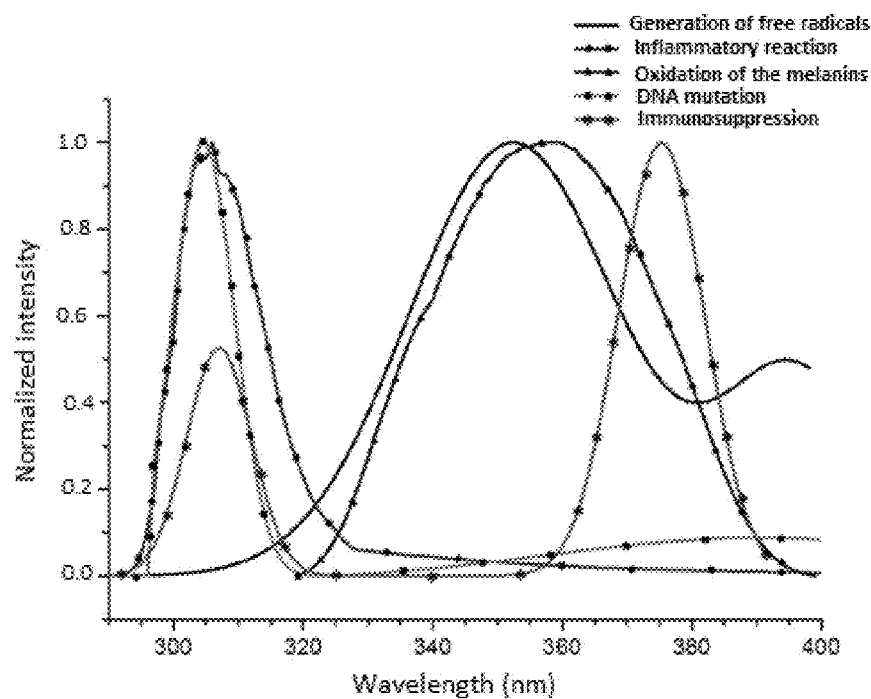
FIG. 5 shows the harmful effects induced by exposure to UV radiation at a normalized intensity as a function of wavelength.

The normalized data is shown in the graph of FIG. 5.

The data shows that the UVB radiation (280 nm to 315 nm) caused an inflammatory reaction, mutations of the DNA, and immunosuppression of the skin tissue. The UVA radiation (315 nm to 400 nm) caused generation of free radicals, oxidation of the melanins and immunosuppression in the cells of the skin.

Figure 6:
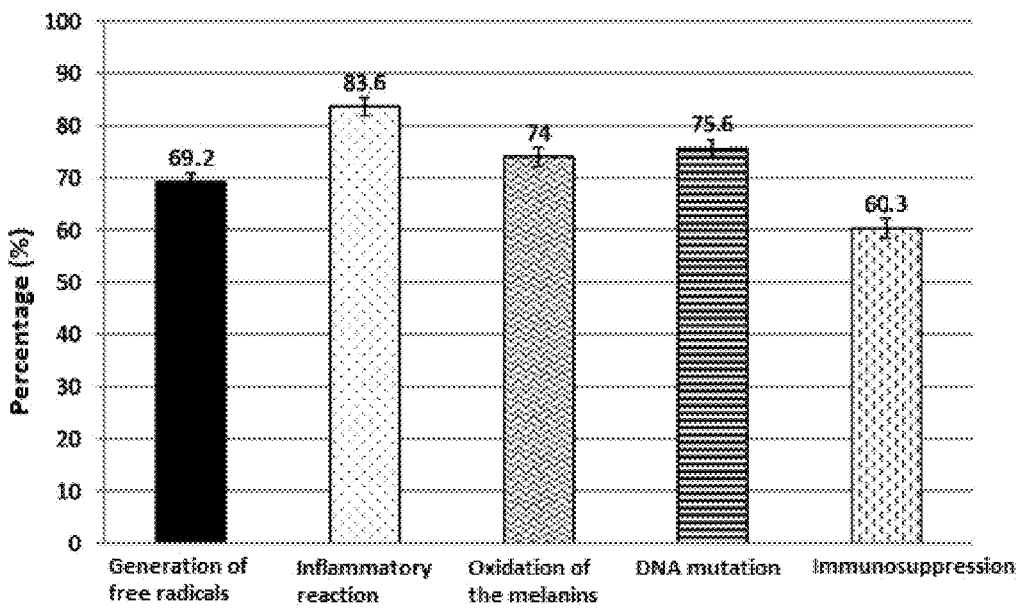
FIG. 6 shows the protective power of the composition of the invention; The error bars correspond to confidence intervals at the 97% confidence level.

The results shown in FIG. 6 show that the composition of the invention makes it possible to reduce certain effects associated with UV radiation:
69.2% less generation of free radicals;
83.6% less inflammatory reaction;
74% less pigmentation of the skin via oxidation of the melanins;
75.6% less mutations of the DNA; and
60.3% less immunosuppression.

The results show that 69.2% of the free radicals generated by exposure to the UV radiation were eliminated. Therefore, only 30.8% of the free radicals could be formed. The protective power computed herein corresponds only to the harmful effects induced by UV radiation.

7/Assessing the Protective Power of the Composition of the Invention Against Generation of Primary and Secondary Free Radicals The trial was performed by the "spin trapping" method coupled with Electron Paramagnetic Resonance (EPR) for conducting trapping experiments in competition by using DIPPMPO (5-(Diisopropoxyphosphoryl)-5-methyl-1-pyrroline-N-oxide) as the trapping molecule. This compound is used conventionally for detecting and studying the superoxide radical using this technique.

The variation in the intensity of the signal of the adduct DIPPMPO-OOH was monitored as a function of time in the presence and in the absence of the creams. The method was assessed by studying the decomposition kinetics of a model radical (TEMPOL or 1-Oxyl-2,2,6,6-tetramethyl-4-hydroxypiperidine) in the presence and in the absence of the creams. Over the duration of the trial, i.e. 20 minutes, no loss of signal from the TEMPOL was observed for the 4 experiments (control+3 samples). Also, control analyses in the presence of Superoxide Dismutase (SOD) were conducted.

TABLE 2

Percentage of inhibition of the DIPPMPO-OOH signal as a function of time.

| Cream | Inhibition at 3 minutes | Inhibition at 5 minutes | Inhibition at 10 minutes | Inhibition at 15 minutes |
|---|---|---|---|---|
| Composition C Mixture of antioxidants: squalane + tocopherol acetate + magnesium ascorbyl phosphate | 48% | 50% | 45% | 53% |
| Composition D Mixture of antioxidants: tocopherol acetate + tocopherol + ergothioneine | 20% | 23% | 37% | 44% |
| Complex Col/AntiOx of the invention (ZnO/3-hydroxy-benzaldehyde) | 100% | 100% | 100% | 100% |

The values indicated in the table are the means of 3 identical experiments (the fluctuations being less than 10%).

Figure 7:
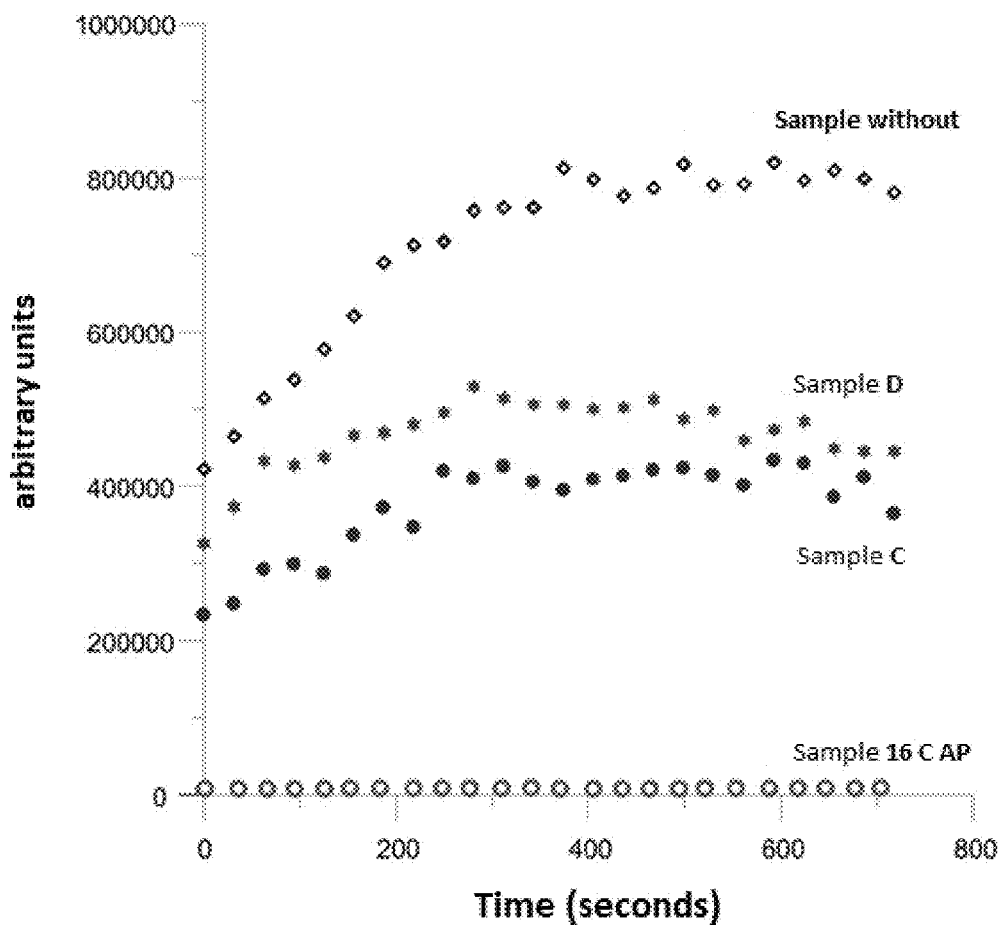
FIG. 7 shows the inhibition of any primary and/or secondary pro-oxidation activity of the colloids functionalized with the antioxidant (Col-2/AntiOx-1) of the invention compared with other antioxidants.

The inhibition kinetics are shown in FIG. 7.

Different superoxide radical trapping properties were observed for each sample.

Composition C showed a reduction of 48% at 3 minutes (53% at 5 minutes) in the signal of the DIPPMPO-00H adduct, suggesting inhibition of half of the oxidizing activity.

Composition D showed a reduction of 20% at 3 minutes (44% at 5 minutes) in the signal of the DIPPMPO-00H adduct, suggesting inhibition that was less effective than the inhibition of the Clinical sample.

For the complex of the invention (the ZnO/3-hydroxybenzaldehyde colloids), no signal corresponding to the DIPPMPO-00H adduct was observed. Thus, all of the superoxide radical produced was trapped.

During these experiments, formation of an additional radical was observed (except for the complex of the invention). According to the Applicant, it appeared that that new radical came from a Haber Weiss reaction or a Fenton reaction involving the presence of transition metal salts available for reacting with the superoxide radical or with the hydrogen peroxide (generated by spontaneous dismutation of the superoxide radical). Thus, the hydroxyl radical would appear to be generated and to react with the constituents of the cream to produce a new radical or "secondary radical", observed in the form of adduct on the DIPPMPO.

In conclusion, the colloids of the invention have capacity greater than the other compounds tested to trap free radicals of the superoxide type. Also, no production of secondary radical species was observed with the colloids of the invention, showing total effectiveness on inhibiting ROS and thus on inhibiting oxidative stress.

8/ Assessing the Antioxidant Activity, Mimicking the Activity of SOD, of the Composition of the Invention The trial was conducted in vitro, and the data was obtained from an experiment with 3 wells per condition (n=3).

8.1 the Superoxide Anion ($O_2 \cdot^-$)

SOD catalyzes the dismutation of the superoxide anion ($O_2 \cdot^-$), into dioxygen ($O_2$) and hydrogen peroxide ($H_2O_2$).

The SOD test is an assay method that, in particular, makes it possible to monitor the reduction of the superoxide anion by conversion of a tetrazolium salt, WST-1, and by production of a dye that is water-soluble, formazan.

The results are shown in FIG. 8A.

These results show that the composition of the invention had activity for dismutation of the superoxide anion that was significant and dose-dependent from +93.7% to +20.1% for concentrations lying in the range 12.5% to 0.2% of the composition of the invention.

8.2 Hydrogen Peroxide ($H_2O_2$)

The SOD test is an assay method that, in particular, makes it possible to monitor the reduction of hydrogen peroxide by conversion of a tetrazolium salt, WST-1, and by production of a dye that is water-soluble, formazan.

The results are shown in FIG. 8B.

These results show that the composition of the invention, at a concentration in the range 25% to 3.12%, induced a significant and dose-dependent inhibition of the $H_2O_2$ radical in the range −22% to −4%.

9/Assessing the Barrier Function of the Composition

The trial was conducted in vivo on an individual for whom 3 regions of 12.5 cm$^2$ were delimited on the anterior faces of the forearms (two regions on the left forearm and one region on the right forearm). The first region constituted the negative control of the trial and was not treated. The second region constituted the positive control of the trial and was treated with 2 mg/cm$^2$ of a commercially available sample. That sample corresponded to the product Collistar® and claimed a "barrier" and moisturizing effect, with specific anti-pollution action against smog, smoke and fine dust. The third region was treated with 2 mg/cm$^2$ of the composition of the invention, the anti-pollution capacity of which was tested.

After 20 minutes of application of the formulations, 40 mg of carbon black (particles having a mean size of 1 μm) were sprinkled onto each of the delimited regions. After a contact time of 5 minutes, the arms were shaken and the residual quantities of carbon black on each of the delimited regions were assessed visually. Each region was then rinsed with 50 mL of distilled water. The residual quantities of microparticles of carbon black were, once again, assessed visually.

Figure 9:
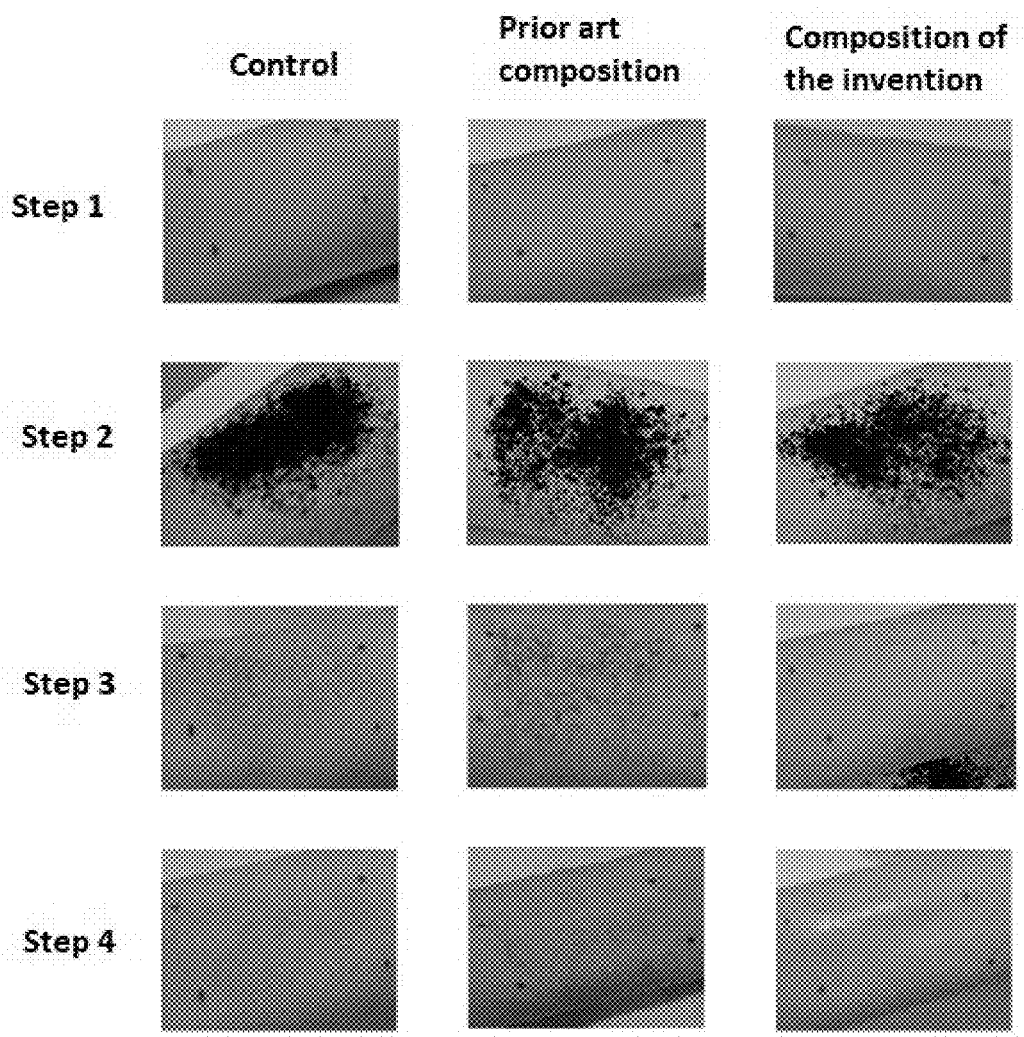
FIG. 9 shows the antiadhesive and repellent effect of the composition of the invention compared with a commercially available composition using the carbon black test.

The results are shown in FIG. 9.

Step 1: Skin regions delimited on the forearms; Application of the products (2 mg/cm-2);

Step 2: Sprinkling 40 mg of carbon black: contact time: 5 minutes;

Step 3: Adhesion test: Residual carbon black after the arm has been shaken; and Step 4: Barrier effect test: Residual carbon black after the skin has been rinsed.

Visually, it was observed that the composition of the invention had better carbon black antiadhesion properties, and a better repellent effect than the negative control (control) and the positive control (prior art composition).

10/Assessing and Quantifying the Repellent Effect of the Composition of the Invention for Repelling the Pollutant Particles and Molecules The experiment protocol as in point 8/ was repeated.

The anterior faces of the forearms were treated by applying 2 mg/cm$^2$ of the composition of the invention (sample B), or of two "anti-pollution" compositions from the prior art (samples A and C).

The quantity of microparticles was quantified before rinsing (T1) and after rinsing (T2).

The barrier effect is determined by measuring the % of detachment after deposition of the microparticles, using the Young-Dupré equation:

$$\cos \theta = \frac{\gamma_{SV} - \gamma_{SL}}{\gamma_{LV}}$$

where $\cos \theta$ represents the attachment of the particles to the determined surface. This parameter makes it possible to determine whether the composition is hydrophilic or hydrophobic; and $\gamma_{SV}$ is the surface tension of the solid/vapor interfaces; $\gamma_{LV}$ is the surface tension of the solid/liquid interfaces; and $\gamma_{LV}$ is the surface tension of the liquid/vapor interfaces.

Figure 10:
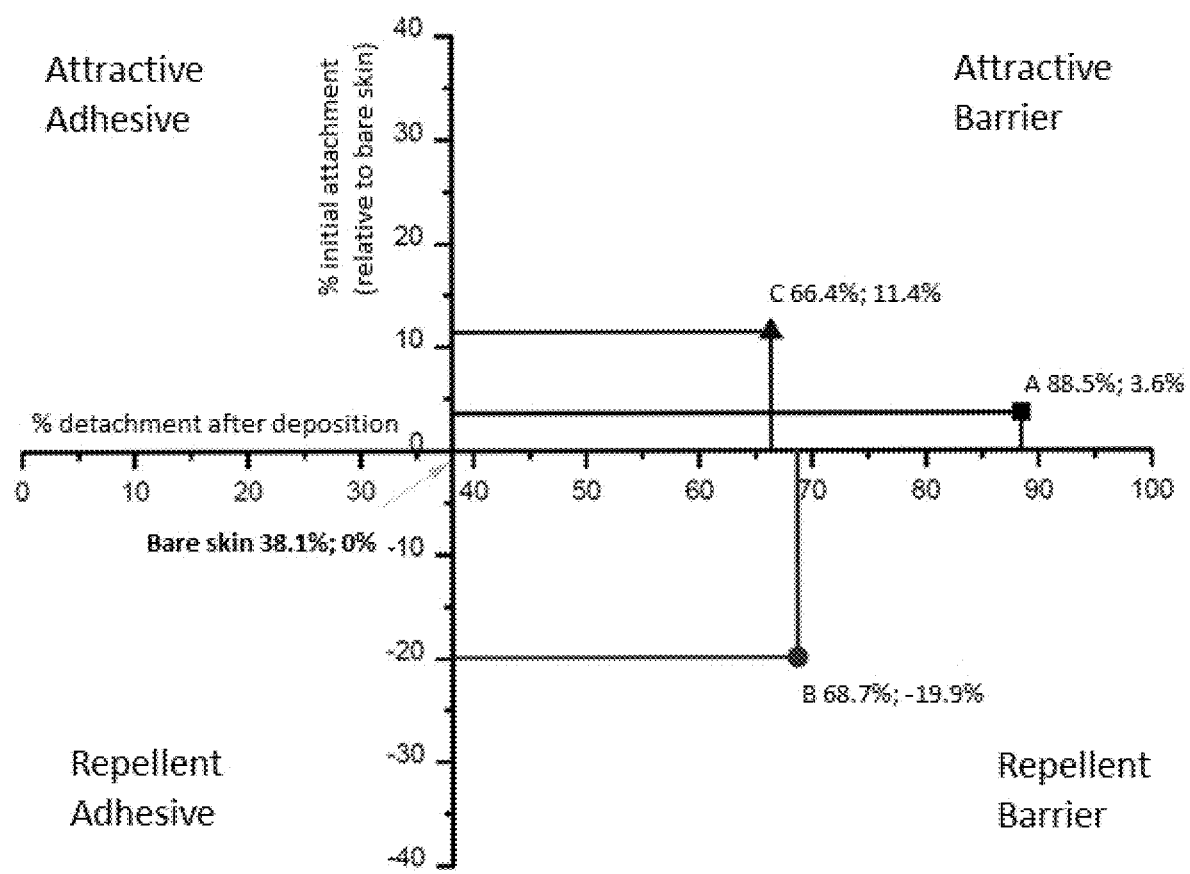
FIG. 10 shows the repellent power of the composition of the invention.

The results are shown in FIG. 10.

The quantification data indicates that applying sample A produced a ratio of "initial attachment to detachment after deposition" of 88.5% before rinsing, and of 3.6% after rinsing. Applying sample C produced a ratio of "initial attachment to detachment after deposition" of 66.4% before rinsing, and of 11.4% after rinsing.

The reduction in the "initial attachment to detachment after deposition" ratio indicates that the prior art products had an antiadhesive property but did not produce any repelling of the microparticles.

Conversely, applying the composition of the invention produced a ratio of "initial attachment to detachment after deposition" of 68.7% before rinsing, and of −19.9% after rinsing. This negative value of the "initial attachment to detachment after deposition" ratio obtained after rinsing clearly illustrates the repellent effect that is supplemented by an antiadhesive effect relative to the microparticles of carbon black.

These results thus show that the composition of the invention has a "barrier" property relative to the microparticles. In other words, the composition of the invention proposes complementary protective effects of antiadhesion and of repellence to atmospheric pollutant particles, and achieves this for the first time.

The invention claimed is:

1. A method of providing topical protection on skin and/or mucous membrane and/or skin appendages, against atmospheric pollutant molecules and against ultraviolet (UV) radiation, said method comprising the steps of:
   a) forming, on skin and/or mucous membranes and/or skin appendages, a polymer matrix that is both repellent and antiadhesive to atmospheric pollutant molecules, by means of a first biocompatible polymer (BP1);
   b) under the effect of UV radiation, photocatalytically degrading the pollutant molecules that have penetrated into the polymer matrix by means of first semiconductor colloids (Col-1) grafted covalently with a second biocompatible polymer (BP2) that is different from the first biocompatible polymer (BP1), thereby leading to formation of free radicals;
   c) neutralizing said free radicals by means of at least 2 antioxidants, namely:

a first antioxidant in the form of second semiconductor colloids (Col-2) grafted covalently with said first antioxidant (AntiOx-1); the second grafted colloids (Col-2) self-regenerating under the action of the UV radiation by the following mechanism:
regeneration of the first antioxidant (AntiOx-1) by transfer of electrons from the second colloids (Col-2) towards said first antioxidant (AntiOx-1); and
regeneration of the second colloids (Col-2) by exposure to UV radiation; and
a second antioxidant (AntiOx-2) that is not in the form of colloids grafted with an antioxidant; and
d) stabilizing the polymer matrix by means of the second antioxidant (AntiOx-2).

2. The method according to claim 1, wherein the second antioxidant is grafted to the first biocompatible polymer.

3. A topical cosmetic composition suitable for implementing the method as defined by claim 1, wherein it comprises:
a first biocompatible polymer;
first colloids grafted with a second biocompatible polymer;
a first antioxidant in the form of second colloids grafted with said first antioxidant; and
a second antioxidant that is not in the form of colloids grafted with an antioxidant.

4. The composition according to claim 3, wherein the second antioxidant is grafted to the first biocompatible polymer.

5. The composition according to claim 3, wherein the semiconductor colloids Col-1 and/or Col-2 are constituted by at least one element chosen from the group consisting of C, Si, Ge, Sn, S, Se, Te, B, N, P, As, Al, Sb, Ga, In, Cd, Zn, O, Cu, Cl, Pb, Tl, Bi, Ti, U, Ba, Sr, Li, Nb, La, I, Mo, Mn, Ca, Fe, Ni, Eu, Cr, Br, Ag, Pt, Hg, and combinations thereof.

6. The composition according to claim 3, wherein the semiconductor colloids Col-1 and/or Col-2 are colloids of zinc oxide, ZnO, or of titanium oxide, $TiO_2$.

7. The composition according to claim 3, wherein:
the first biocompatible polymer is a polysaccharide;
the first and second colloids are colloids of zinc oxide or colloids of rutile titanium dioxide, $TiO_2$;
the second biocompatible polymer is chosen from the group consisting of polyvinylpyrrolidone, polyvinyl acetate, polyvinyl alcohol, polyvinyl chloride, styrenics, polyamides, acrylates, and mixtures thereof; and
the first antioxidant and/or the second antioxidant are chosen from the group consisting of phenolic aldehyde or phenolic acid and complexes thereof.

8. The composition according to claim 3, wherein the polysaccharide is pullulan.

9. The composition according to claim 3, wherein the second biocompatible polymer is polyvinylpyrrolidone.

10. The composition according to claim 3, wherein the second semiconductor colloids Col-2 grafted covalently with a first antioxidant AntiOx-1 are formed of:
second colloids Col-2 that are colloids of zinc oxide, ZnO, or of titanium oxide, $TiO_2$;
a first antioxidant AntiOx-1 that is a phenolic aldehyde or a phenolic acid; and
a covalent grafting in the form of a spacer arm positioned between Col-2 and AntiOx-1, the spacer arm comprising in the range 1 to 8 carbons, and having an alkoxysilane function capable of binding itself covalently to the colloid Col-2 and a function of the hydroxyl type, of the phosphate type, or of the amine type capable of binding itself to the antioxidant AntiOx-1.

11. The composition according to claim 3, wherein:
the first antioxidant AntiOx-1 is chosen from the group consisting of 2-hydroxybenzaldehyde 3-hydroxybenzaldehyde, 4-hydroxybenzaldehyde, and 3,4 dihydroxybenzaldehyde; and
the spacer arm is 3-(aminopropyl)triethoxysilane.

12. The composition according to claim 3, wherein the second antioxidant AntiOx-2 is gallic acid.

13. The composition according to claim 3, wherein:
the first biocompatible polymer is pullulan grafted with gallic acid and represents in the range 0.1% by mass of the composition to 20% by mass of the composition;
the first colloids are zinc oxide colloids grafted with PVP and represent in the range 0.1% by mass of the composition to 30% by mass of the composition; and
the second colloids are colloids of zinc oxide grafted with phenolic aldehyde or phenolic acid or complexes thereof, and represent in the range 0.1% by mass of the composition to 10% by mass of the composition.

14. The composition according to claim 3, wherein the composition further comprises at least one additive chosen from the group consisting of humectant agents, viscosity control agents, and water.

15. The composition according to claim 3, wherein the composition further comprises:
glycerol representing in the range 0.1% by mass to 20% by mass of the composition;
guar gum representing in the range 0.1% by mass to 20% by mass of the composition; and
water representing in the range 30% by mass to 99.5% by mass of the composition.

16. A composition according to claim 7, wherein the first antioxidant is different from the second antioxidant.

17. A composition according to claim 16, wherein the polysaccharide is pullulan.

18. A composition according to claim 17, wherein the second biocompatible polymer is polyvinylpyrrolidone.

19. A composition according to claim 3, wherein the second semiconductor colloids Col-2 grafted covalently with a first antioxidant AntiOx-1 are formed of:
second colloids Col-2 that are colloids of zinc oxide, ZnO, or of titanium oxide, $TiO_2$;
a first antioxidant AntiOx-1 that is a phenolic aldehyde or a phenolic acid; and
a covalent grafting in the form of a spacer arm positioned between Col-2 and AntiOx-1, the spacer arm comprising in the range 2 to 4 carbons, and having an alkoxysilane function capable of binding itself covalently to the colloid Col-2 and a function of the hydroxyl type, of the phosphate type, or of the amine type capable of binding itself to the antioxidant AntiOx-1.

20. A composition according to claim 13, wherein:
the first biocompatible polymer is pullulan grafted with gallic acid and represents in the range 0.8% by mass to 5% by mass;
the first colloids are zinc oxide colloids grafted with PVP and represent in the range 5% by mass to 9% by mass; and
the second colloids are colloids of zinc oxide grafted with phenolic aldehyde or phenolic acid or complexes thereof, and represent in the range 0.6% by mass to 2% by mass.

* * * * *

UNITED STATES PATENT AND TRADEMARK OFFICE
CERTIFICATE OF CORRECTION

| | | |
|---|---|---|
| PATENT NO. | : 11,801,208 B2 | Page 1 of 1 |
| APPLICATION NO. | : 17/251050 | |
| DATED | : October 31, 2023 | |
| INVENTOR(S) | : Athalin et al. | |

It is certified that error appears in the above-identified patent and that said Letters Patent is hereby corrected as shown below:

On the Title Page

In the Foreign Application Priority Data (30): Insert -- May 31, 2018 (FR) 1854745 --

Signed and Sealed this
Nineteenth Day of December, 2023

Katherine Kelly Vidal
*Director of the United States Patent and Trademark Office*